United States Patent
Draheim (12)

(10) Patent No.: US 6,325,991 B1
(45) Date of Patent: Dec. 4, 2001

(54) METHODS AND COMPOSITIONS FOR TREATING PERIODONTAL DISEASE WITH AN INHIBITOR OF SECRETORY PHOSPHOLIPASE $A_2$

(76) Inventor: Susan E. Draheim, 6125 Burlington Ave., Indianapolis, IN (US) 46220

(*) Notice: Subject to any disclaimer, the term of this patent is extended or adjusted under 35 U.S.C. 154(b) by 0 days.

(21) Appl. No.: 09/382,711

(22) Filed: Aug. 24, 1999

Related U.S. Application Data

(60) Provisional application No. 60/097,682, filed on Aug. 24, 1998.

(51) Int. Cl.⁷ .............................. A61K 7/16; A61K 9/68; A61F 2/02
(52) U.S. Cl. .............................. 424/49; 424/48; 424/435; 424/440; 424/422; 424/426; 424/484; 514/419; 514/900; 514/902
(58) Field of Search .................................. 424/49–58, 48, 424/435, 440, 422, 426, 486; 514/152, 419, 900, 902

(56) References Cited

U.S. PATENT DOCUMENTS

| | | | |
|---|---|---|---|
| 4,355,022 | * 10/1982 | Rabussay | 424/50 |
| 4,764,377 | 8/1988 | Goodson . | |
| 4,892,736 | 1/1990 | Goodson . | |
| 4,919,981 | 4/1990 | Cole et al. . | |
| 4,933,182 | 6/1990 | Higashi et al. . | |
| 4,938,763 | * 7/1990 | Dunn et al. | 604/891.1 |
| 5,077,049 | * 12/1991 | Dunn et al | 424/426 |
| 5,186,936 | 2/1993 | Groves . | |
| 5,223,248 | * 6/1993 | McNamara et al. | 424/49 |
| 5,242,910 | 9/1993 | Damanj . | |
| 5,302,374 | 4/1994 | Wagner . | |
| 5,324,519 | * 6/1994 | Dunn et al. | 424/426 |
| 5,324,520 | * 6/1994 | Dunn et al. | 424/435 |
| 5,328,682 | 7/1994 | Pullen et al. . | |
| 5,368,859 | * 11/1994 | Dunn et al. | 424/426 |
| 5,433,952 | * 7/1995 | Sipos | 424/489 |
| 5,523,297 | * 6/1996 | Pruzanski et al. | 514/152 |
| 5,578,634 | 11/1996 | Bach et al. | 514/419 |
| 5,614,223 | * 3/1997 | Sipos | 424/489 |
| 5,622,498 | 4/1997 | Brizzolara et al. . | |
| 5,641,800 | 6/1997 | Bach et al. | 514/415 |
| 5,654,326 | 8/1997 | Bach et al. | 514/419 |
| 5,663,059 | 9/1997 | Hawkins et al. | 534/69.2 |
| 5,684,034 | 11/1997 | Bach et al. | 514/419 |
| 5,733,923 | 3/1998 | Bach et al. | 514/419 |
| 5,770,588 | * 6/1998 | McNamara et al. | 514/152 |
| 5,882,631 | 3/1999 | Suga et al. . | |
| 5,916,606 | 6/1999 | Record et al. . | |
| 5,919,602 | 7/1999 | Herr et al. . | |
| 5,919,774 | 7/1999 | Bach et al. | 514/91 |
| 5,919,810 | 7/1999 | Bach et al. | 514/419 |
| 5,919,943 | 7/1999 | Bach et al. | 548/447 |
| 5,925,335 | 7/1999 | Shuch et al. . | |

OTHER PUBLICATIONS

Abstracts of Bulkacz et al (I) Microbios Lett. 10(38): 79–88 Phospholepose A ISSN: 0307–5494 Activity of Microorganisms from Plaque Cuden Miledm CAPLUS 1980: 403530 93:3530, 1979.*

Bulkacz et al. (II) J. Periodont. Res. 20(2):146–153 "Phospholipose A ISSN:0022–3484 Activity of Extra Cellular Products from Bacteroides Coden JPD Ray Melonenogonecus Epithelcal Tissue Cultures" CAPLUS 1985: 420 714 103: 20714.*

Shinohara et al Shikoku Shigakkai Zasshi 11(2) 201–216 "The Role ISSN: 0914–6091 and Regaultions of Phospholipase A2 in Penudoskles"Coden: SSZAED (In Japanese) CAPLUS 1999:137039 130:279938, 1999.*

Medical Plastics and Biomaterials Magazine/MPB Article Index; Nov. 1997; Polymers in Controlled Drug Delivery, Lisa Brannon–Peppas.

Draheim, Susan E. et al., "Indole Inhibitors of Human Nonpancreatic Secretory Phospholipase $A_2$. 3. Indole–3–glyoxamides", *Journal of Medicinal Chemistry*, vol. 39, No. 26., pp 5159–5175 (1996).

Dillard, Robert D. et al., "Indole Inhibitors of Human Nonpancreatic Secretory Phospholipase $A_2$. 2. Indole–3–acetamides with Additional Functionality", *Journal of Medicinal Chemistry*, vol. 39, No. 26, pp 5137–5158 (1996).

Dillard, Robert D. et al., "Indole Inhibitors of Human Nonpancreatic Secretory Phospholipase $A_2$. 1. Indole–3–acetamides",*Journal of Medicinal Chemistry*, vol. 39, No. 26, pp 5119–5136 (1996).

Fleisch, Jerome H. et al., "Recombinant Human Secretory Phospholipase $A_2$ Released Thromboxane from Guinea Pig Bronchoalveolar Lavage Cells: In Vitro and Ex Vivo Evaluation of a Novel Secretory Phospholipase $A_2$ Inhibitor", *The Journal of Pharmacology and Experimental Therapeutics*, vol. 278, No. 1, pp 252–257 (1996).

Golub, L.M., Ryan, M.E., and Williams, R.C., "Modulation of the Host Response in the Treatment of Periodontitis", *Dentistry Today*, Oct. 1998.

Wery, J.P. et al., "Structure of Recombinant Human Rheumatoid Arthritic Synovial Fluid Phospholipase $A_2$ at 2.2 A Resolution," *Nature*, No. 352, Jul. 4, 1991.

Schevitz, R. W. et al., "Structure–based Design of the First Potent and Selective Inhibitor of Human Non–Pancreatic Secretory Phospholipase $A_2$", *Nature Structural Biology*, vol. 2, No. 6., Jun. 1995.

\* cited by examiner

*Primary Examiner*—Shep K. Rose
(74) *Attorney, Agent, or Firm*—Woodard, Emhardt, Naughton, Moriarty & McNett

(57) ABSTRACT

The present invention relates to methods of treating periodontal disease in a mammal. The methods include administering to an animal an s effective amount of an inhibitor of $sPLA_2$. The inhibitors may be advantageously delivered as a composition that includes various carriers. In certain aspects of the invention, inhibitors used in the method include substituted indole or substituted pyrrole $sPLA_2$ inhibitors. Also provided are compositions that include the $sPLA_2$ carriers for oral delivery of the inhibitors.

24 Claims, No Drawings

METHODS AND COMPOSITIONS FOR TREATING PERIODONTAL DISEASE WITH AN INHIBITOR OF SECRETORY PHOSPHOLIPASE $A_2$

REFERENCE TO RELATED APPLICATIONS

The present application claims the benefit of U.S. Provisional Patent Application Ser. No. 60/097,682, filed on Aug. 24, 1998, which is hereby incorporated by reference in its entirety.

BACKGROUND OF THE INVENTION

Periodontal disease is an oral inflammatory disease that begins when inflammation of gingival tissues (gingivitis) progresses to an inflammation of the periodontal attachment tissues. This inflammation may eventually lead to breakdown of the periodontal attachment, periodontal pocket formation and bone loss-periodontitis. The disease may progress to the extent of causing tooth loss due to destruction of the tooth supporting bone. A similar course of events can take place in the tissues surrounding dental implants (peri-implantitis), and can result in gradual loosening and eventual loss of the implant.

The rate of progression of periodontal disease is extremely variable. It is believed to be modulated by a complex interaction between subgingival bacterial, the host defense system (including immune and inflammatory responses), and other local tissue factors. Methods of treatment, however, have traditionally focused on the bacterial component of the disease.

The conventional approach to the treatment of periodontal disease involves initially removing subgingival bacterial plaque and calculus deposits with scaling and root planing procedures and following-up with improved oral hygiene procedures. If this treatment does not halt progression of the disease, surgical reduction of periodontal tissues is often performed, with the intention of decreasing the depth of the periodontal pocket, thus decreasing the area available for bacterial colonization and aiding mechanical removal of the microorganisms. Concurrent treatment with an antibacterial agent may also be used to further reduce bacterial numbers.

Antibiotics such as tetracycline derivatives are commonly used. These drugs are either administered systemically, or, more recently, they are introduced directly into the periodontal pocket by site-specific drug delivery methods utilizing a polymeric matrix material as a carrier. Such products include Atridox® and Actisite®. Another agent, chlorohexidine gluconate (an antiseptic) has been formulated into a gelatin/glutaraldehyde matrix in the form of a small chip, the Periochip®, which delivers a bactericidal dose of chlorohexidine to the periodontal pocket. With these methods, drug concentrations in the periodontal pocket are much higher than could be attained by systemic dosing. These systems provide a sustained release of the drug in the periodontal pocket over a 7 to 10 day course of treatment. They are more difficult to administer than an oral antibacterial agent, but by delivering a high, sustained dose over the course of treatment, the site-specific systems are less likely to cause bacterial resistance development, which is problematic with long-term systemic antimicrobial treatment.

While these systems offer a possible alternative to periodontal surgery for treatment of refractory sites that have not responded to scaling and root planing procedures, the overall strategy of treatment of periodontal disease with antibacterial agents alone may be questioned. Although periodontal disease may be initiated by the presence of certain microorganisms, the present invention recognizes that it is an inflammatory condition that may be more effectively treated by attempting to decrease or eliminate the inflammatory response to the bacteria rather than the bacteria itself.

A variety of non-steroidal anti-inflammatory drugs (NSAIDs) have been studied as treatments for periodontal disease. These studies have examined NSAIDs delivered either topically, site-specifically or systemically and some have been found to exhibit limited beneficial effects. However, the NSAIDs only block the cyclooxygenase pathway in the metabolism of arachidonic acid, thereby blocking formation of only a portion of the inflammatory mediators. When used systemically, NSAIDs also may cause gastrointestinal side effects, which would be prohibitive for long-term treatment. No NSAID is currently marketed specifically for the treatment of periodontal disease.

Recently, Periostat® has been introduced for the treatment of periodontal disease. Periostat® is a low-dose formulation of doxycycline. Although doxycycline is known for its antimicrobial properties, at the low dosages present in Periostat®, its effects are due to inhibition of collagenase enzymes. Periostat® shows no antibacterial activity at the prescribed dosage. The clinical studies show results similar to those obtained with local delivery of antibacterial agents.

The current methods for treatment of periodontal disease are costly, painful and often ineffective, discouraging many from seeking treatment. Of all the above-mentioned products, none provide a significant impact on the treatment of periodontal disease. A need therefore exists for such a product. The compositions and methods described herein addresses this need.

SUMMARY OF THE INVENTION

Periodontal disease is highly prevalent and its progression can not always be arrested by scaling, root planing and oral hygiene procedures. In these cases, alternatives or adjuncts to surgical treatment of periodontal disease are highly desired. Traditionally, these alternatives have been limited to antibacterial agents. However, antibacterial treatment has proven to be unpredictable and often ineffective. Although it is understood that bacteria are a necessary component of the disease, the presence of suspected pathogenic bacteria does not automatically mean periodontal disease will develop. If the disease does develop, there may be quiescent periods and exacerbations even when the bacterial levels are relatively constant. The present invention proposes an approach that addresses the inflammatory aspect of the disease and suggests that the inflammatory response to the bacteria is the main factor both in the development and the progression of the disease state and a more appropriate target of treatment than the bacteria.

The microorganisms that have been implicated in periodontal disease are gram-negative, anaerobic bacteria. These characteristics may be more important than identifying the specific causative bacterial strain due to the host effects they cause. All gram-negative bacteria have endotoxin present in their cell wall. When the gram-negative, anaerobic bacteria present in the subgingival spaces die, endotoxins present in the bacterial cell wall are released into the gingival sulcus. These toxins cause minimal tissue damage on their own. More importantly, host cells respond to the endotoxin by secreting a variety of inflammatory mediators (e.g., cytokines), which are capable of recruiting and maintaining inflammatory cells at a tissue site. Cytokines act on host cells causing overexpression and secretiorn of secretory phospholipase $A_2$ (s$PLA_2$).

The enzyme sPLA$_2$ catalyzes hydrolysis of the sn-2 ester bonds of membrane phospholipids to liberate lysophospholipids and fatty acids, including arachidonic acid. Lysophospholipids have the ability to damage cells and membranes, but the arachidonic acid causes a cascade of events. Arachidonic acid is metabolized by two enzymatic pathways and subsequently converted to proinflammatory substances including leukotrienes (via lipoxygenase activity), thromboxanes and prostaglandins (both via cyclooxygenase activity). These chemical mediators recruit cells of the immune system and the compliment cascade to produce an exaggerated inflammatory response. In the periodontum, progressive tissue and eventually bone destruction may result if these processes get out of control. The invention described herein proposes that this is the core of the pathogenesis of periodontal disease, and that attenuating or eliminating the inflammatory response is the key to the treatment of the disease. The present invention thus provides inhibitors of SPLA$_2$ in order to prevent release of arachidonic acid from membrane phospholipids, to stop the entire arachidonic acid cascade and thereby stop the destruction attributed to the inflammatory process.

Differences in the tendency of individuals to produce sPLA$_2$ when subjected to bacterial endotoxin may explain the variability in periodontal disease progression between individuals with similar local host factors (e.g., plaque and calculus deposits). Variability in sPLA$_2$ levels may also explain individuals who experience episodic active and inactive disease phases, with the disease being most active when sPLA$_2$ is most actively produced. The present invention provides a potent inhibitor of SPLA$_2$ in order to halt progression of the disease.

Accordingly, other features of the invention include methods of treating periodontal disease in a mammal. The methods may include administering an effective amount of an inhibitor of sPLA$_2$ to a mammal in need of treatment. A wide variety of inhibitors of sPLA$_2$ may be advantageously used in the invention. In certain forms of the invention, the inhibitors used in the method are selected from 1H-indole-3-acetamides, 1H-indole-3-acetic acid hydrazides, 1H-indole-3-glyoxylamides, related structures and mixtures thereof. In other embodiments of the invention, the inhibitors are selected from 1H-indole-1-acetamides, 1H-indole-1-acetic acid hydrazides, 1H-indole-1-glyoxylamides, related structures, and mixtures thereof. In further embodiments, the inhibitors are selected from substituted pyrroles. Other inhibitors of sPLA$_2$ may also be advantageously used in the present invention, especially those having similar sPLA$_2$ inhibitory activity as the inhibitors particularly described herein.

The inhibitors of the invention are advantageously delivered in various carriers by a variety of routes. For example, the inhibitors may be delivered systemically by an oral route, or directly to the periodontal pocket. The preferred carrier for direct delivery is a matrix such as a fiber, chip or film made from a biocompatible polymeric material sized for introduction into the periodontal pocket. In one form of the invention, the polymeric material is biodegradeable but may also be non-biodegradeable and removed after the treatment. The matrix may be formed into a device for treating periodontal disease in a mammal, wherein the matrix is impregnated with an effective amount of an inhibitor of sPLA$_2$. In yet other embodiments, the inhibitor may be delivered topically to the oral cavity in a composition that includes a carrier such as a toothpaste, mouthwash, or chewing gum. The chewing gum typically includes a gum base of a biocompatible polymeric material such as an elastomer. Moreover, the inhibitor may be delivered to the periodontal pocket by flushing the periodontal pocket with a composition that includes an oral irrigation solution carrier.

Other features of the invention include compositions for treating periodontal disease in a mammal. The inhibitors may be selected from those described above that are combined with a carrier as described above.

It is an object of the invention to provide compositions and effective methods for treating periodontal disease.

This and other objects and advantages of the present invention will be apparent from the descriptions herein.

DESCRIPTION OF THE PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates generally to compositions that include sPLA$_2$ inhibitors and methods of using the compositions for the treatment of periodontal disease. A wide variety of sPLA$_2$ inhibitors may be advantageously used in the present invention. The inhibitors used in the present invention are small organic molecule pharmaceutical agents that are hereby defined as having a molecular weight of no greater than about 1000 g/mole. The molecular weight of the inhibitors is typically about 300 to about 900 g/mole. Inhibitors of the 1H-indole-3-glyoxylamide, 1H-indole-3-acetamide, and 1H-indole-3-acetic acid hydrazide structural types, and related structures, as particularly described in U.S. Pat. Nos. 5,578,634; 5,654,326; 5,684,034; 5,733,923; 5,919,810; and 5,919,943 may be utilized, as well as 1H-indole-1-acetamide, 1H-indole-1-acetic acid hydrazide, and 1H-indole-1-glyoxylamide structural types, and related structures, as particularly described in U.S. Pat. No. 5,641,800. Other examples of inhibitors that may be advantageously used in the invention include substituted pyrroles as particularly described in U.S. Pat. No. 5,919,774. These inhibitors, as well as other small molecule pharmaceutical agents of similar inhibitory potency, and pharmaceutically acceptable salts, solvates, or prodrugs thereof, are preferred for use in the invention.

In certain aspects of the invention, the inhibitors may be provided in a composition that includes a carrier which allows the inhibitor to be placed directly into the peridontal pocket. This carrier may be, for example, a biocompatible polymeric material which may be retained in the periodontal pocket for the duration of treatment or the carrier may be a solution which would be used to irrigate the periodontal pocket, thus with limited retentive properties. For example, the substituted indole or substituted pyrrole sPLA$_2$ inhibitors described above, or mixtures thereof, may be in a composition that includes a carrier. Other carriers include those that may be applied topically to the oral cavity, including a chewing gum carrier that includes a biocompatible polymeric material such as an elastomer, a toothpaste carrier, a mouthwash carrier or a solution used to irrigate the periodontal pocket. In other aspects of the invention, the inhibitors and compositions of the present invention may be advantageously used in a method of treating periodontal disease in a mammal, the method including administering to a mammal an effective amount of the specified inhibitor of sPLA$_2$. In certain forms of the method, it is preferred to administer the inhibitors systemically by an oral route in carriers known to the art and described herein.

For the chemical structures described herein, certain defining terms are employed as follows.

The term "alkyl" means an aliphatic hydrocarbon which may be either straight chain or branched and includes, for example, methyl, ethyl and structural isomers of propyl, butyl, pentyl and hexyl.

The term "alkenyl" as used herein refers to a straight or branched hydrocarbon group having one double bond and includes, for example, vinyl, propenyl, crotonly, isopentyl, butenyl, and isomers thereof.

The term "alkynyl" as used herein refers to a straight or branched hydrocarbon group having one triple bond, and includes, for example, ethynyl, propynyl, 1-butynyl and isomers thereof.

The term "hydrocarbyl" means an organic group containing only carbon and hydrogen.

The term "halo" means fluoro, chloro, bromo or iodo.

The term "acidic group" means an organic group which, when attached to an indole nucleus through suitable linking atoms (hereinafter defined as the "acid linker"), acts as a proton donor capable of hydrogen bonding. Examples of such acidic groups include 5-tetrazolyl, SO$_3$H and the following:

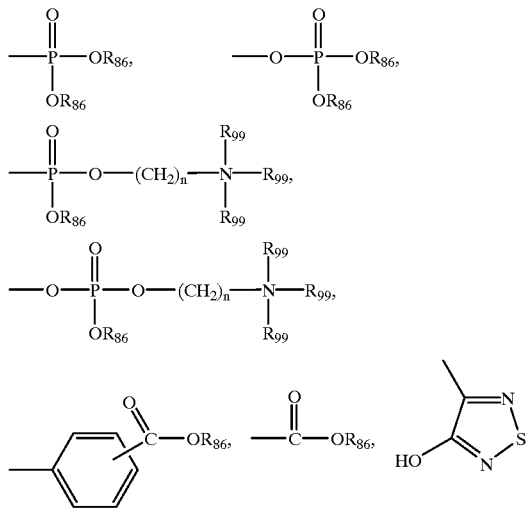

where n is 1 to 8, $R_{86}$ is independently selected from a hydrogen, a metal or $C_1$-$C_{10}$ alkyl and $R_{99}$ is hydrogen or $C_1$-$C_{10}$ alkyl.

The term "acid linker" refers to a divalent linking group symbolized as "—$(L_a)$—", which has the function of joining the 4, 5, 6 and/or 7 position of the indole nucleus to an acidic group, or other group as specified herein, through the linking group [i.e., indole nuclei—$(L_a)$—acidic group].

The term "acid linker length" refers to the number of atoms (excluding hydrogen) in the shortest chain of the linking group —$(L_a)$— that connects the 4,5, 6 or 7 position of the indole nucleus with the acidic group. The presence of a carbocyclic ring in —$(L_a)$— counts as the number of atoms approximately equivalent to the calculated diameter of the carbocyclic ring. Thus, a benzene or cyclohexane ring in the acid linker counts as 2 atoms in calculating the length of —$(L_a)$—. Examples of acid linker groups advantageously incorporated into the inhibitor include:

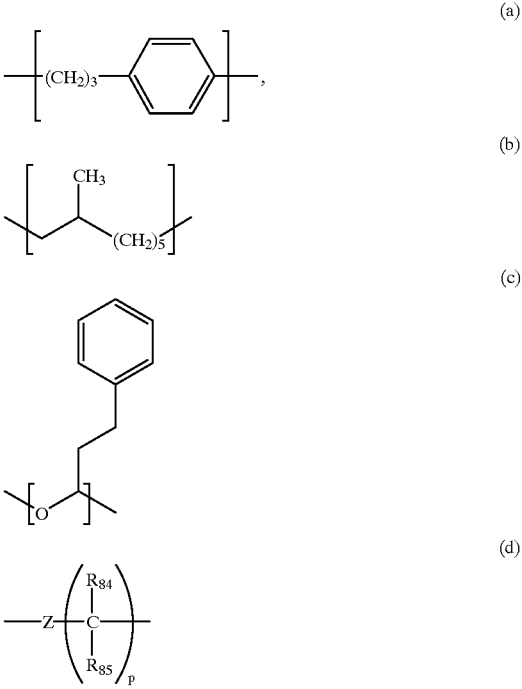

wherein
$R_{84}$ and $R_{85}$ are each independently selected from hydrogen, $C_1$-$C_{10}$ alkyl, hydroxy, or $R_{84}$ and $R_{85}$ taken together are ═;
is 1 to 8;
Z is a bond, O, N($C_1$-$C_{10}$ alkyl), N(H), or S.

It can be seen that (a), (b) and (c) have acid linker lengths of 5, 7, 2, and respectively, whereas the acid linker length of (d) will vary depending on p.

The term "amine" includes primary, secondary and tertiary amines.

The term "metal" includes metals known to the art, and especially those that may form salts such as alkali metals, including lithium sodium, and potassium, and alkaline earth metals, such as calcium and magnesium.

The term "carbocyclic radicals" is defined herein to mean radicals derived from a saturated or unsaturated, substituted or unsubstituted 5 to 14 membered organic nucleus whose ring forming atoms are solely carbon atoms. Examples of carbocyclic radicals include cycloalkyl, cycloalkenyl, phenyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, anthracenyl, biphenyl, bibenzyzlyl and bibenzylyl homologues represented by the following formula:

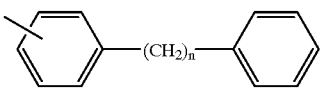

wherein n is from 1 to 8.

The term "heterocyclic radical" refers to radicals derived from monocyclic or polycyclic, saturated or unsaturated, substituted or unsubstituted heterocyclic nuclei having 5 to 14 rings atoms and containing from 1 to 3 heteroatoms selected from the group consisting of nitrogen, oxygen or sulfur. Examples of such heterocyclic radicals include pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1,2-A)pyridinyl, benzotriazolyl, anthranilyl, 1,2-benzisoxazolyl, benzoxazolyl, benzotriazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl and quinoxalinyl. The heterocyclic radicals may be substituted by non-interfering substituents.

The term "non-interfering substituents" refers to radicals suitable for substitution at positions 4, 5 6 and/or 7 on the indole nucleus (i.e., those positions that are substituted by $R_4$, $R_5$, $R_6$, and $R_7$ respectively), on the heterocyclic radicals and carbocyclic radicals defined herein or at other locations specified herein. Examples of such non-interfering substituents include $C_1$-$C_6$ alkyl, $C_2$-$C_6$ alkenyl, $C_2$-$C_6$ alkynyl, $C_7$-$C_{12}$ aralkyl, $C_7$-$C_{12}$ alkaryl, $C_3$-$C_8$ cycloalkyl, $C_3$-$C_8$ cycloalkenyl, phenyl, tolulyl, xylenyl, biphenyl, $C_1$-$C_6$ alkoxy, $C_2$-$C_6$ alkenyloxy, $C_2$-$C_6$ alkynyloxy, $C_2$-$C_{12}$alkoxyalkyl, $C_2$-$C_{12}$ alkoxyalkyloxy, $C_2$-$C_{12}$ alkylcarbonyl, $C_2$-$C_{12}$alkylcarbonylamino, $C_2$-$C_{12}$ alkoxyamino, $C_2$-$C_{12}$ alkoxyaminocarbonyl, $C_2$-$C_{12}$alkylamino, $C_1$-$C_6$ alkylthio, $C_2$-$C_{12}$ alkylthiocarbonyl, $C_0$-$C_6$ alkylsulfinyl, $C_1$-$C_6$ alkylsulfonyl, $C_2$-$C_6$ haloalkoxy, $C_1$-$C_6$ haloalkylsulfonyl, $C_1$-$C_6$haloalkyl, $C_1$-$C_6$ hydroxyalkyl, C(O)O($C_1$-$C_6$ alkyl), $(CH_2)n$—O—($C_1$-$C_6$ alkyl), benzyloxy, phenoxy, phenylthio,—($CONHSO_2R_{10}$), —CHO, amino, amidino, carbamyl, carboxyl, carbalkoxy, halo, $(CH_2)_n$—$CO_2H$, cyano, cyanoguanidinyl, guanidino, hydrazide,hydrazino, hydrazido, hydroxy, hydroxyamino, nitro, phosphono, $SO_3H$, thioacetal, thiocarbonyl and $C_1$-$C_6$ carbonyl, wherein n is from 1 to 8 and $R_{10}$ is hydrogen, $C_1$-$C_{10}$ alkyl or a metal.

In a first aspect of the invention, compositions for treating periodontal disease in a mammal are provided that include an effective amount of an inhibitor of $sPLA_2$ in a carrier, such as a biocompatible polymeric material. In a first embodiment, the inhibitor has the following structure:

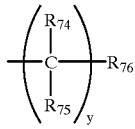

(I)

or a pharmaceutically acceptable salt or prodrug derivative thereof,
wherein
$R_1$ is selected from the groups (a), (b), (c) or (d) wherein:
(a) is $C_4$-$C_{20}$ alkyl, $C_4$-$C_{20}$ alkenyl, $C_4$-$C_{20}$ alkynyl, carbocyclic radicals or heterocyclic radicals;
(b) is a member of (a) substituted with one or more independently selected non-interfering substituents;
(c) is the group —(L)—($R_{80}$) where —(L)— is a divalent linking group of 1 to 12 atoms selected from carbon, hydrogen, oxygen, nitrogen, and sulfur wherein the combination of atoms in —(L)— are selected from the group consisting of (i) carbon and hydrogen only, (ii) sulfur only, (iii) oxygen only, (iv) nitrogen and hydrogen only, (v) carbon, hydrogen and sulfur only; and where $R_{80}$ is a group selected from (a) or (b);
(d) is a group having the formula:

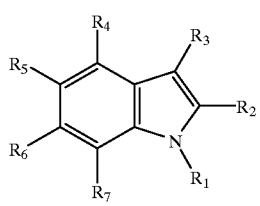

wherein
each $R_{74}$ and $R_{75}$ are independently selected from hydrogen, hydroxy, or $C_1$-$C_{10}$ alkyl, or $R_{74}$ and $R_{75}$ taken together are ===; $R_{76}$ is aryl or aryl substituted by halo, cyano, -CHO, hydroxy, nitro, phenyl, SH, $C_1$-$C_{10}$ alkyl, $C_1$-$C_{10}$ alkoxy, $C_1$-$C_{10}$ alkylthio, amino, hydroxyamino, or a 5 to 8 membered unsubstituted heterocyclic ring or substituted with a non-interfering substituent;
y is1 to 8;
$R_2$ is hydrogen, halo, $C_1$-$C_3$ alkyl, $C_2$-$C_3$ alkenyl, $C_1$-$C_2$ alkylthio, $C_1$-$C_3$ alkoxy, C2-C3 alkenyloxy, C2-C3 alkynyloxy, C3-C4 cycloalky, C3-C4 cycloalkenyl, cyano, —CHO, amino, amidino, carbamyl, carboxyl, methylsulfinyl, hydrazino, hydrazido, $C_1$-$C_2$ hydroxyalkyl, thiocarbonyl or $C_1$-$C_2$ carbonyl;
$R_3$ is

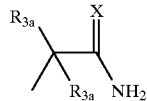

(Group 1)

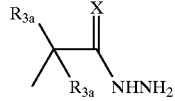

(Group 2)

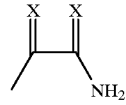

(Group 3)

wherein
each $R_{3a}$ is independently hydrogen, halo, or $C_1$-$C_3$ alkyl and X is oxygen or sulfur;
$R_4$, $R_5$, $R_6$, R7 are each independently hydrogen, phenoxy, halo, hydroxy, $C_1$-$C_{10}$ alkyl, $C_2$-$C_{10}$ alkenyl, $C_2$-$C_{10}$ alkynyl, $C_3$-$C_8$ cycloalkyl, aryl, aralkyl, $C_1$-$C_{10}$ haloalkyl, $C_1$-$C_{10}$ alkoxy, $C_1$-$C_{10}$ haloalkoxy, $C_4$-$C_8$ cycloalkoxy, $C_1$-$C_{10}$ alkylthio, arylthio, thioacetal, —C(O)O($C_1$-$C_{10}$ alkyl), carboxyl, hydrazide, hydrazino, hydrazido, amino, nitro, SH, cyano, —$NR_{82}R_{83}$ and —$C(O)NR_{82}R_{83}$, where $R_{82}$ and $R_{83}$ are independently hydrogen, $C_1$-$C_{10}$ alkyl, $C_1$-$C_{10}$ hydroxyalkyl, or taken together with N, form a 5 to 8-membered heterocyclic ring; or any two adjacent hydrocarbyl groups in the set $R_4$, $R_5$, $R_6$, $R_7$, combine with the ring carbon atoms to which they are attached to form a 5 or 6 membered unsubstituted carbocyclic ring, or substituted with a non-interfering substituent; or the group —($L_a$)—Q wherein —($L_a$)— is an acid linker having an acid linker length of 1 to 10 and Q is —$CON(R_{82}R_{83})$, or an acidic group selected from 5-tetrazolyl, SO₃H, or the following:

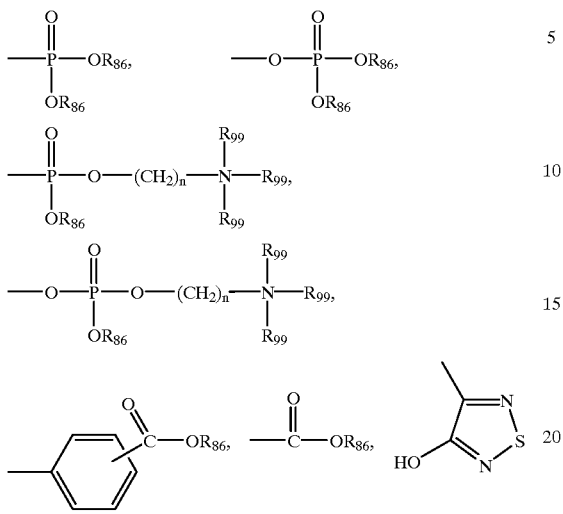

wherein n is 1 to 8, $R_{82}$ and $R_{83}$ are as defined above, $R_{86}$ is independently selected from a metal or $C_1$-$C_{10}$ alkyl and $R_{99}$ is hydrogen or $C_1$-$C_{10}$ alkyl. The 5 to 8 membered heterocyclic ring may be selected from those heterocyclic radicals as described herein. Moreover, the 5 to 6 membered carbocyclic rings include those 5 to 6 membered carbocyclic radicals described herein. The above compounds substituted at the 3 position on the indole nucleus with groups 1, 2 or 3 as described above are hereinafter referred to as 3-substituted indoles.

It is further preferred that $R_4$ or $R_5$ is the group —($L_a$)—Q, wherein the acid linker —($L_a$)— is a group having the formula:

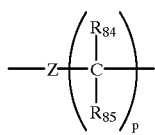

Group D wherein, $R_{84}$ and $R_{85}$ are each independently selected from hydrogen, $C_1$-$C_{10}$ alkyl, hydroxy, or $R_{84}$ and $R_{85}$ taken together are ==;

p is 1 to 8; and

Z is a bond, O, N($C_1$-$C_{10}$ alkyl), N(H), or S; and Q is an acidic group or —C(O)NR$_{82}$R$_{83}$ as defined in the first embodiment. Examples of divalent linking groups —(L)— for R, include:

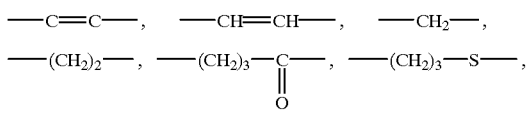

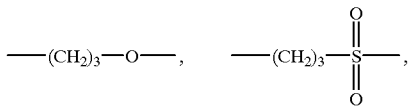

In a second embodiment of the invention, structure I may be substituted as follows:

$R_1$ and $R_2$ are as defined in the first embodiment;

$R_3$ is group 1, wherein $R_{3a}$ and X are as defined above for the first embodiment;

$R_4$, $R_5$, $R_6$, $R_7$ are as described above in the first embodiment.

Another preferred group of 3-substituted indoles include those wherein:

$R_1$ and $R_2$ are as defined in the first embodiment;

$R_3$ is group 1, wherein $R_{3a}$ and X are as defined above for the first embodiment;

$R_4$ and $R_5$ are each independently selected from (i) and (ii) where;
  (i) is hydrogen, halo, alkyl, or alkoxy; and
  (ii) is the group —($L_a$)—Q, wherein —($L_a$)—is group D as described above, provided that at least one of $R_4$ or $R_5$ must be selected from (ii) and where $R_{84}$, $R_{85}$, p, Z, Q, $R_{82}$, $R_{83}$, n, $R_{86}$ and $R_{99}$ are as defined above in the first embodiment; and $R_6$ and $R_7$ are as defined for the first embodiment described above.

Other preferred 3-substituted indoles include those wherein structure 1 is substituted as follows:

$R_1$ is a benzyl group that may be unsubstituted or substituted with non-interfering substituents;

$R_2$ is methyl, ethyl, cyclopropyl, cyano or halo;

$R_3$ is group 1 as described above, wherein each $R_{3a}$ is as described in the first embodiment above and X is oxygen;

$R_4$ and $R_5$ are each independently selected from (i) and (ii) where;
  (i) is hydrogen, halo, alkyl, or alkoxy; and
  (ii) is the group —($L_a$)—Q, wherein —($L_a$)—is group D as described above, provided that at least one of $R_4$ or $R_5$ must be selected from (ii) and where $R_{84}$ and $R_{85}$ are independently, hydrogen or $C_1$-$C_3$ alkyl; p is from 1 to 4; Z is O; Q is an acidic group; and $R_6$ and $R_7$ are non-interfering substituents.

Another preferred subclass of 3-substituted indoles include those where:

$R_1$ and $R_2$ are as defined in the first embodiment;

$R_3$ is group 2 as described above, wherein $R_{3a}$ and X are as defined above for the first embodiment.

$R_4$, $R_5$, $R_6$ and $R_7$ are as defined in the first embodiment.

In yet other embodiments, structure I may be substituted as follows:

$R_1$ and $R_2$ are as defined in the first embodiment;

$R_3$ is group 2 as described above, wherein $R_{3a}$ and X are as defined 25 for the first embodiment;

$R_4$ and $R_5$ are each independently selected from (i) and (ii) wherein:
  (i) is hydrogen, halo, alkyl, or alkoxy; and
  (ii) is group D as above, provided that at least one of $R_4$ or $R_5$ must be selected from (ii) and where $R_{84}$, $R_{85}$, p, Z, Q, $R_{82}$, $R_{83}$, n, $R_{86}$ and 30 RgP are as defined above in the first embodiment; and $R_6$ and $R_7$ are as defined in the first embodiment.

In further embodiments, structure 1 may be substituted as follows:

$R_1$ and $R_2$ are as defined in the first embodiment;

$R_3$ is group 3 as described above, wherein X is defined as above for the first embodiment.

$R_4$, $R_5$, $R_6$ and $R_7$ are as defined in the first embodiment.

In yet further embodiments, structure 1 is substituted as follows:

-R and $R_2$ are as defined in the first embodiment;

$R_3$ is group 3, wherein X is as defined above for the first embodiment;

$R_4$ and $R_5$ are each independently selected from (i) and (ii) where;

(i) is hydrogen, halo, alkyl, or alkoxy; and (ii) is the group —$(L_a)$—Q, wherein —$(L_a)$—is group D as described above for the first embodiment, provided that at least one of $R_4$ or $R_5$ must be selected from (ii) and where $R_{84}$, $R_{85}$, p, Z, Q, $R_{82}$, $R_{83}$, n, $R_{86}$ and $R_{99}$ are as defined above in the first embodiment; and $R_6$ and $R_7$ are as defined for the first embodiment described above.

In more preferred embodiments, a 3-substituted indole is provided wherein:

$R_1$ is a benzyl group that may be unsubstituted or substituted with non-interfering substituents;

$R_2$ is methyl, ethyl, cyclopropyl, cyano or halo;

$R_3$ is group 3 as described above, wherein X is oxygen;

$R_4$ is —$(L_a)$—Q, wherein —$(L_a)$—is group D as described above; $R_{84}$ and $R_{85}$ are hydrogen or $C_1$-$C_3$ alkyl; p is from 1 to 2, Z is 0; and Q is an acidic group as defined above; and $R_5$, $R_6$ and $R_7$ are non-interfering substituents as described above.

The 3-substituted indoles described above, including the 1H-indole-3-acetamides, 1H-indole-3-acetic acid hydrazides and the 1H-indole-3-glyoxylamides may be synthesized by methods known to the art and as particularly described in U.S. Pat. Nos. 5,684,034; 5,578,634; 5,654,326; 5,733,923; 5,919,810 and 5,919,943, all to Bach et al.

In yet other forms of the invention, the inhibitors are indoles substituted at the 1 position on the indole nucleus with groups 1, 2 or 3 described above (hereinafter referred to as 1-substituted indoles). These indoles have the following structure:

(I)

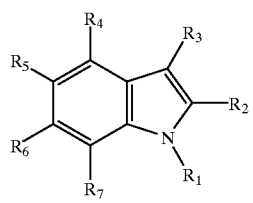

wherein $R_1$ is

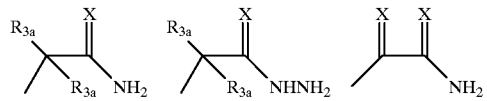

wherein
each $R_{3a}$ is independently hydrogen, halo, or $C_1$-$C_3$ alkyl and X is oxygen or sulfur;

$R_2$ is hydrogen, halo, $C_1$-$C_3$ alkyl, $C_3$-$C_4$ cycloalkyl, $C_3$-$C_4$ cycloalkenyl, $C_1$-$C_2$ alkoxyl, $C_1$-$C_2$ alkylthio or is a non-interfering substituent selected from the group consisting of cyano, amino, amidino, halo, carbamyl, carboxyl, $C_2$-$C_3$ alkenyl, $C_1$-$C_3$ alkyl, cyclopropyl, cyclopropenyl, $C_1$-$C_3$ alkoxy, $C_1$-$C_2$ alkenyloxy, $C_2$-$C_3$ alkynyloxy, C, alkylsulfinyl, hydrazino, $C_1$-$C_2$ hydroxyalkyl, thiocarbonyl, and $C_1$-$C_2$ carbonyl, or other non-interfering substituent that may include hydrogen that has 1 to 3 atoms other than hydrogen;

$R_3$ is selected from groups (a), (b) and (c) wherein:

(a) is $C_7$-$C_{20}$ alkyl, $C_7$-$C_{20}$ alkenyl, $C_7$-$C_{20}$ alkynyl, carbocyclic radicals or heterocyclic radicals;

(b) is a member of (a) substituted with one or more non-interfering substituents, or (c) is the group —(L)—$R_{80}$ wherein —(L)—is a divalent linking group of 1 to 12 atoms selected from carbon, hydrogen, oxygen, nitrogen, and sulfur wherein the combination of atoms in —(L)—are selected from the group consisting of (i) carbon and hydrogen only, (ii) sulfur only, (iii) oxygen only, (iv) nitrogen and hydrogen only, (v) carbon, hydrogen and sulfur only; and where $R_{80}$ is a group selected from (a) or (b);

$R_4$ and $R_5$ are each independently selected from hydrogen, non-interfering substituent, carbocyclic radical, carbocyclic radical substituted with non-interfering substituents, heterocyclic radical and heterocyclic radical substituted with non-interfering substituents;

$R_6$ and $R_7$ are independently selected from hydrogen, a non-interfering substituent, or the group —$(L_a)$— (acidic group) wherein —$(L_a)$—is an acid linker having an acid linker length of 1 to 10. In this embodiment, it is preferred that at least one of $R_6$ and $R_7$ is the group —$(L_a)$—(acidic group). Unless otherwise indicated, the non-interfering substituents, carbocyclic radicals and heterocyclic radicals are as described according to the definitions above.

For the 1-substituted indoles, it is preferred that, when $R_3$ is —(L)—, —(L)—is selected from those groups as described for —(L)—in the 3-substituted indoles described above.

Furthermore, preferred $R_{80}$ substituents are selected from the carbocyclic radicals as described above. Particularly preferred substituents for $R_3$ are selected from the following groups:

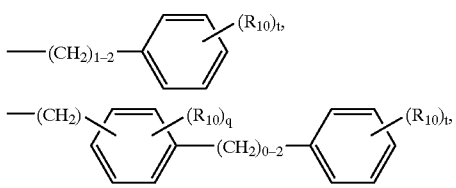

wherein $R_{10}$ is a radical independently selected from halo, $C_1$-$C_{10}$ alkyl, $C_1$-$C_{10}$ alkoxy, S-($C_1$-$C_{10}$ alkyl) and $C_1$-$C_{10}$ haloalkyl, q is a number from 0 to 4 and t is a number from 0 to 5.

Another preferred class of compounds is where $R_7$ is an acid linker having a linker length 2 or 3, and the acid linker group, —$(L_a)$—for $R_7$ is selected from the group represented by the following formula:

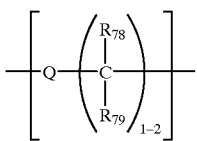

wherein:
Q is selected from the group $CH_2$, O, N(H), and S, and $R_{78}$ and $R_{79}$ are each independently selected from hydrogen, $C_1$-$C_{10}$ alkyl, aryl, $C_1$-$C_{10}$ alkaryl, $C_1$-$C_{10}$ alkaryl, carboxy, ethoxycarbonyl, and halo.

It is most preferred for $R_7$ that the acid linker —$(L_a)$— is selected from the following groups:

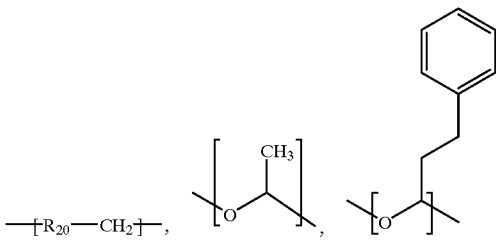

wherein
$R_{20}$ is O, S, N($R_{21}$), $CH_2$; and $R_{21}$ is hydrogen or a $C_1$-$C_4$ alkyl.

Yet another preferred subclass of 1-substituted indoles are those wherein $R_6$ has an acid linker substituent with an acid linker length of 3 to 10 atoms, and the acid linker group, —$(L_a)$— for $R_6$ is selected from:

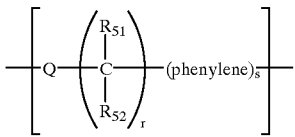

wherein r is a number from 1 to 7, s is 0 or 1, Q is selected from the group $CH_2$, O, N(H), and S; and $R_{51}$, and $R_{52}$ are each independently selected from hydrogen, $C_1$-$C_{10}$ alkyl, aryl, $C_1$-$C_{10}$ alkaryl, carboxy, ethoxycarbonyl, and halo. Most preferred are compounds where the acid linker, —$(L_a)$— for $R_6$ is selected from the following groups:

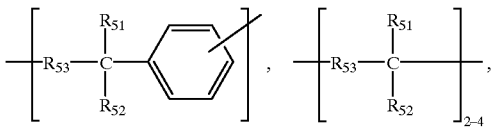

wherein
$R_{53}$ is hydrogen or $C_1$-$C_4$ alkyl, $R_{51}$ and $R_{52}$ are each independently selected from hydrogen, $C_1$-$C_{10}$ alkyl, aryl, $C_1$-$C_{10}$ alkaryl, $C_1$-$C_{10}$ aralkyl, carboxy, ethoxycarbonyl and halo.

The 1-substituted indoles may be prepared by methods known to the art, and as particularly described in U.S. Pat. No. 5,641,800 to Bach et al.

In yet another aspect of the invention, compositions for treating periodontal disease are provided that include an effective amount of an inhibitor of sPLA$_2$, in a pharmaceutically acceptable carrier, such as a carrier that may be administered directly to the periodontal pocket, wherein the inhibitors are substituted pyrroles having the following formula:

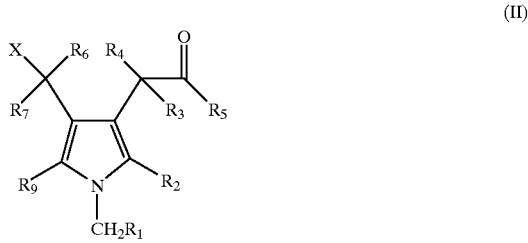

or a pharmaceutically acceptable salt thereof,
wherein
$R_1$ is hydrogen, $C_1$-$C_4$ alkyl, phenyl or phenyl substituted with one or two substituents selected from the group consisting of $C_1$-$C_4$ alkyl, $C_1$-$C_4$ alkoxy, phenyl($C_1$-$C_4$)alkyl, $C_1$-$C_4$ alkylthio, halo and phenyl;

$R_2$ is hydrogen, $C_1$-$C_4$ alkyl, halo, $C_1$-$C_4$ alkoxy, or $C_1$-$C_4$ alkylthio;

$R_3$ and $R_4$ are each hydrogen, or when taken together are ==;

$R_5$ is amino or NHNH$_2$;

$R_6$ and $R_7$ are each hydrogen; or when one of $R_6$ and $R_7$ is hydrogen, the other is $C_1$-$C_4$ alkyl or $(CH_2)_n$—$R_{10}$ wherein $R_{10}$ is $CO_2R_{11}$, $PO_3(R_{11})_2$, $PO_4(R_{11})_2$ or $SO_3R_{11}$ wherein $R_{11}$ is independently hydrogen or $C_1$-$C_4$ alkyl and n is 1 to 4; or $R_6$ and $R_7$, taken together, are ==or =S;

X is $(C_1$-$C_6)$alkyl or $(C_2$-$C_6)$alkenyl which are substituted with $R_8$;or is phenyl substituted at the ortho position with $R_8$ or additionally optionally substituted with one or two substituents selected from the group consisting of hydrogen, $C_1$-$C_4$ alkyl, halo, $C_1$-$C_4$ alkoxy, or two substituents, when taken together with the phenyl group to which they are attached, form a naphthyl group; wherein $R_8$ is —$(CH_2)$,—$R_{10}$ and $R_{10}$, $R_{11}$ and n are as defined above; and $R_9$ is hydrogen or $C_1$-$C_4$ alkyl.

Preferred substituted pyrroles are where:
$R_1$ is phenyl; $R_2$ is methyl or ethyl; $R_5$ is amino; $R_6$ and $R_7$ are each hydrogen; X is $(C_1$-$C_6)$alkyl that may be substituted with $R_8$; or is phenyl substituted at the ortho position with $R_8$, wherein $R_8$ is $CO_{02}R_{11}$ and $R_{11}$ is as defined above; and $R_9$ is methyl or ethyl.

The substituted pyrroles may be prepared by methods known to the art, and as particularly described in U.S. Pat. No. 5,919,774 to Bach et al.

Included within the scope of the invention is the use of pharmaceutically acceptable salts of the compounds included above. Pharmaceutically acceptable salts are known in the art and include alkali and alkaline earth salts such as lithium, sodium, potassium, calcium, magnesium and aluminum. Salts are typically prepared from the free acid by treating the acid in solution with a base or by exposing the acid to an ion exchange resin.

Further included within the invention is the use of inhibitors of the invention that possess one or more chiral centers which may exist in optically active forms. Moreover, when the inhibitors include an alkenyl or alkenylene group, there exists the possibility of cis- and trans-isomeric forms of the inhibitors. The use of R- and S-isomers and mixtures thereof, including racemic mixtures as well as mixtures of cis-and trans-isomers, are also within the scope of this invention. Additional asymmetric carbon atoms may be present in a substituent group such as an alkyl group. Use of all such isomers, as well as mixtures thereof, are contemplated. If a particular stereoisomer is desired, it can be prepared by methods well know to the art, including use of stereospecific reactions with starting materials which contain the asymmetric centers and are already resolved.

Further included within the invention is the use of prodrug derivative derivatives of the compounds described above. Prodrugs are derivatives of the compounds of the invention which have chemically or metabolically cleavable groups and become, either by solvolysis or under physiological conditions, the compounds of the invention which are pharmaceutically active in vivo. Prodrugs include acid derivatives known to the art, such as esters prepared by reaction of the parent acidic compound with a suitable alcohol, or amides prepared by reaction of the parent compound with a suitable amine. Simple aliphatic or aromatic esters derived from acidic groups pendent on the compounds of this invention are preferred prodrugs.

The compositions of the present invention include a pharmaceutically acceptable carrier, preferably for systemic oral delivery. Any suitable carrier known in the art may be used. Carriers may be a solid, liquid or a mixture of a solid and a liquid. The carriers may take the form of capsules, tablets, pills, powders lozenges, suspensions, emulsions or syrups. The carriers may include substances that act as a flavoring agents, lubricants, solubilizers, suspending agents, binders, stabilizers, tablet disintegrating agents and encapsulating materials.

Tablets for systemic oral administration may include excipients, as known in the art, such as calcium carbonate, sodium carbonate, sugars (e.g., lactose, sucrose, mannitol, sorbitol), celluloses (e.g., methyl cellulose, sodium carboxylmethyl cellulose), gums (e.g., arabic, tragacanth), together with disintegrating agents, such as maize, starch or alginic acid, binding agents, such as gelatin, collagen or acacia and lubricating agents, such as magnesium stearate, stearic acid or talc.

In powders, the carrier is a finely divided solid which is mixed with an effective amount of a finely divided inhibitor.

In solutions, suspensions or syrups, an effective amount of the inhibitor is dissolved or suspended in a carrier such as sterile water or an organic solvent, such as aqueous propylene glycol. Other compositions can be made by dispersing the inhibitor in an aqueous starch or sodium carboxylmethyl cellulose solution or a suitable oil known to the art.

In preferred forms of the invention, compositions for direct delivery of the inhibitor to the periodontal pocket may include solid carriers, such as polymers, fibers, chips and films. The solid carriers may advantageously be formed into a matrix that is configured, or sized, for introduction into a periodontal pocket. The matrix, or other solid carrier, which is impregnated with the inhibitor, is typically retained in the periodontal pocket and allows release of the inhibitor. Such matrices, impregnated with an inhibitor of $sPLA_2$, may thus advantageously form a device for treating periodontal disease. The carriers may alternatively be a liquid or a gel, and may be formulated to allow retention of the drug in the periodontal pocket by, for example, solidifying. Such compositions or devices for direct delivery may be placed directly in the periodontal pocket and left in place over the treatment period to achieve a therapeutic effect. The carriers may be biodegradable and may be allowed to degrade, or may alternatively be removed at the end of the treatment period.

In one embodiment, an effective amount of an inhibitor of $sPLA_2$ may be combined with, or dispersed in, a carrier formed from a biocompatible polymeric material. A wide variety of biocompatible materials for delivery of therapeutic agents to the oral cavity are known in the art. For example, such polymers may be selected from cellulosic polymers, collagen, glycolic acid polymers, methacrylate polymers, ethylene vinyl acetate copolymers, ethylene vinyl alcohol copolymers, polylactides and polycaprolactone. The polymer may furthermore be an elastomer whose solid form may be advantageously used in forming a chewing gum carrier. Moreover, when the polymeric material is in the form of a solid, such as a fiber, chip or film, the polymeric material is preferably impregnated with the inhibitor.

In one preferred form of the invention, a composition for direct oral delivery includes an $sPLA_2$ inhibitor, or mixture of inhibitors, described above which is combined with a biodegradeable gel formulation based on polylactides, such as poly(DL)lactide. A wide variety of such formulations are known to the art and include, for example, a carrier including a poly(DL)lactide dissolved in a solvent, such as N-methyl-2-pyrrolidone. Such a carrier is available commercially under the product name Atrigel®. The carrier may include, for example, about 37% of a poly(DL)lactide dissolved in about 63% N-methyl-2-pyrrolidone.

In a preferred embodiment, typically when periodontal pockets are of a sufficient depth (e.g., 5 mm or more), a composition for direct oral delivery includes the inhibitors described above which are delivered with a solid carrier in the form of a chip that includes a biodegradable matrix of hydrolyzed gelatin that is cross-linked with glutaraldehyde and further includes glycerin and water. Such solid carrier chips are used to deliver an antibacterial agent in a product marketed under the name Periochipo. In the present case, the chip is typically impregnated with the inhibitor and is placed in the periodontal pocket.

In those embodiments wherein the polymer is an elastomer, the elastomer may serve as the gum base for a chewing gum carrier. Chewing gum, as known in the art, contains an insoluble chewable gum base portion and a water-soluble bulk portion with various fillers and flavoring agents. The insoluble gum base may include the various elastomers, elastomer solvents, plasticizers, waxes, emulsifiers and inorganic fillers as known in the art and as described, for example, in U.S. Pat. No. 5,916,606 to Record et al. A wide variety of natural and synthetic elastomers known to the art may advantageously be used. The elastomers in the insoluble gum base portion may include, for example, styrene butadiene copolymers, both natural and synthetic, and natural elastomers such as rubbers, guayule, and gums such as chicle, jelutong, balata, and lechi capsi. The water-soluble portion may include softeners, sweeteners and flavoring agents known to the art.

In yet other forms of the invention, compositions are provided that include the inhibitor dispersed in other carriers, including a toothpaste carrier, solutions for oral irrigation of periodontal pockets or a mouthwash carrier.

A wide variety of toothpaste formulations are known to the art, and as shown, for example, in U.S. Pat. No. 5,302,374 to Wagner. The formulations typically include sodium fluoride, water, an abrasive such as hydrated silica, and carriers such as glycerin, a sugar flavoring agent such as xylitol or sorbitol, sodium lauryl sulfate, cellulose gum, sodium saccharin or other flavoring agent, titanium dioxide and a base, such as sodium carbonate.

A wide variety of mouthwash formulations are also known to the art and as shown, for example, in U.S. Pat.

Nos. 4,919,918 to Harrison et al. and 5,328,682 to Pullen et al. A mouthwash formulation may typically include coloring agents, flavoring agents, such as sorbitol, xylitol or saccharin, alcohol or other antibacterial agents as known in the art. The mouthwash may also include sterile water, glycerin and polyethylene glycol. Although the formulation may be alcohol-based, formulations that are alcohol-free and based on, for example, acids and surface active agents may advantageously be used. Such alcohol-free formulations are well known in the art, and as described, for example, in U.S. Pat. No. 4,919,918.

A wide variety of oral irrigation solutions known to the art may be used. For example, such solutions may include sterile water, glycerin and polyethylene glycol.

Other carriers known to the art may also be used, and include, for example, ointments for topical delivery into which the inhibitor is dispersed.

In yet other forms of the invention, compositions are provided that include the inhibitors described herein, along with one or more antibacterial compounds known to the art. Examples of such antibacterial compounds include chlorhexidine gluconate, iodine, sulfonamides, mercurials, phenolics, and antibiotics such as tetracycline, neomycin, kanamycin, doxycycline and metronidazole.

The compositions include amounts of the respective inhibitors effective in treating periodontal disease. This therapeutic amount may vary, depending on the extent of periodontal disease, the route of administration, the potency of the inhibitor and whether other inhibitors are administered. However, the compositions may typically include an amount of the inhibitor to provide a daily dose of about 0.001 mg/kg to about 50 mg/kg of body weight of the inhibitor. Of course, lower or higher dosages may be needed depending on the specific case. As a tablet or capsule, typical unit dosage forms range from 0.01 mg to about 1 g.

The inhibitors of the invention are effective in inhibiting $sPLA_2$ and are thus effective in inhibiting release of the fatty acid arachidonic acid. The inhibitors preferably inhibit $sPLA_2$ by at least about 30%, preferably at least about 50% and most preferably at least about 90%. Methods to determine the degree to which $sPLA_2$ is inhibited are well known to the art, and include, for example, assays which directly measure free $sPLA_2$ levels (i.e., $sPLA_2$ not bound to an inhibitor) or the levels of other inflammatory mediators.

In yet another aspect of the invention, methods for treating periodontal disease are provided. The methods include administering to a mammal in need of treatment, such as a mammal with periodontal disease, an effective amount of the inhibitors described above. The inhibitors may be delivered with a carrier as described above.

The inhibitor may be delivered by several routes. For example, the inhibitor may be delivered systemically by oral administration, typically with carriers in the form of pills, tablets, lozenges, suspensions, emulsions or syrups as described above. The inhibitors may also be administered directly to the periodontal pocket. For example, the inhibitors may be delivered site-specifically to the periodontal pocket with the use of gel and the various polymer carriers described above. The polymer or other matrix carriers are advantageous in that they allow a high concentration and a controlled release of the inhibitor over a period of time.

A wide variety of mammals may be treated, including cats, dogs and preferably humans.

Administration of the compositions directly into the periodontal pocket, such as by placing a matrix carrier impregnated with an inhibitor in the periodontal pocket, is preferably performed after completion of scaling and root planing procedures, but may also be accomplished without performing such procedures.

When administering the inhibitors in a liquid carrier, such as an oral irrigation solution, the solution may be used to flush the periodontal pocket. The solution may be administered directly to the periodontal pocket by syringe, as an irrigant solution for an ultrasonic scaler or by other appropriate methods of delivery known to the art.

The mammal is typically treated with an effective amount of the inhibitor. This amount will depend on the factors mentioned above.

Moreover, the duration of the treatment will also depend on the factors mentioned above, as well as on the ability of the particular carrier to sustain release of the drug. For biodegradable carriers, the treatment period will also be based on the retentive ability of the carrier.

The effectiveness of the various compositions administered for periodontal disease in a mammal can be determined by measuring changes in various periodontal parameters known in the art after a period of treatment with the compositions compared to treatment with scaling and root planing procedures alone, or no treatment at all. For example, probing depth measurements and radiographic analysis are standard analyses for monitoring the progression of periodontal disease.

Periodontal probing measurements can record pocket depth (i.e., the distance from the gingival margin to the depth of the gingival sulcus), or loss of attachment (i.e., the distance from the cementoenamel junction to the depth of the gingival sulcus).

Radiographic analyses use standardized radiographs to determine changes in bone height (based on linear measurements) and bone mass (based on radiographic density measurements).

Other measures of disease severity include gingival indices, which assign scores to gingival sites based on the appearance or degree of inflammation or the amount of bleeding upon probing. However, the other methods described above are less subjective and thus more preferred.

As stated above, only selected examples of inhibitors that may be advantageously used in the compositions and methods of the present invention are discussed herein. Other inhibitors of $sPLA_2$ known to the skilled artisan that are not specifically mentioned herein may also be used in the present invention, and preferably include inhibitors having similar $sPLA_2$ inhibitory activity as the inhibitors described herein. Furthermore, the compositions described herein may also be advantageously used to treat inflammation of tissue surrounding dental implants, known as peri-implantitis, using the same procedures described herein.

Reference will now be made to specific examples illustrating the compositions and methods described above. It is to be understood that the examples are provided to illustrate preferred embodiments and that no limitation to the scope of the invention is intended thereby.

EXAMPLE 1

Inhibitor/Gel Carrier Composition

A bioresorbable flowable polymeric formulation can be made by dissolving poly(DL)lactide in N-methyl-2-pyrrolidone to form a solution of 63% by weight N-methyl-2-pyrrolidone and 37% by weight poly(DL)lactide. An effective amount of the inhibitor can be combined with the carrier.

The method of delivery can include placing the above formulation in one syringe and including an effective amount of the sPLA$_2$ inhibitor (in a second pharmaceutically inert carrier as described above) in a second syringe. After mixing, the viscous material may be applied to the periodontal pocket where it will solidify upon contact with the gingival crevicular fluid. The drug can be released over a 7 to 10 day period in a concentration sufficient to achieve inhibition of sPLA$_2$ as the carrier biodegrades.

EXAMPLE 2

Inhibitor/Ethylene Vinyl Acetate Copolymer Fiber Carrier Composition

Any of the substituted indoles, pyrroles or other sPLA$_2$ inhibitors may be delivered with an ethylene vinyl acetate copolymer carrier. In order to form an inhibitor/fiber carrier composition, effective amounts of the inhibitor may be combined with ethylene vinyl acetate copolymer and the composition can be extruded through the chamber of a Tinius Olsen Extrusion Plastometer. The chamber is typically heated to a temperature below that at which the inhibitor decomposes. After the extrusion, the extruded material is then cooled to form fibers. The fibers can be about 0.1 mm to about 1 mm in diameter.

EXAMPLE 3

Inhibitor/Toothpaste Composition

The toothpaste can include about 65% to about 90% by weight of a base component that includes about 5–20% by weight water, about 10 to about 40% by weight glycerin, about 20 to about 40% by weight of calcium carbonate and about 20 to about 40% by weight silica. The toothpaste can include an effective amount of an sPLA$_2$ inihibitor.

While the invention has been illustrated and described in detail in the foregoing description, the same is to be considered as illustrative and not restrictive in character, it being understood that only the preferred embodiment has been shown and described and that all changes and modifications that come within the spirit of the invention are desired to be protected. For example, although a method of treating periodontal disease utilizing the various inhibitors and compositions is described herein, other oral inflammatory diseases may also be amenable for such treatment, including peri-implantitis. Therefore, a method of treating peri-implantitis, or other oral inflammatory diseases, utilizing the inhibitors and compositions described herein is also encompassed within this invention. In addition, all references cited herein are indicative of the level of skill in the art and are hereby incorporated by reference in their entirety.

What is claimed is:

1. A method of treating periodontal disease in a mammal, comprising:

administering to said mammal in need of treatment an effective amount of an inhibitor of secretory phospholipase A$_2$.

2. The method of claim 1, wherein said inhibitor has the following structure:

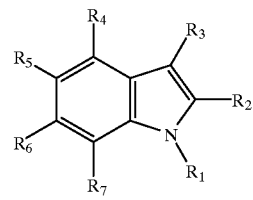

(I)

or a pharmaceutically acceptable salt, or prodrug derivative thereof
wherein
R$_1$ is selected from the groups (a), (b), (c) or (d) wherein:
(a) is C$_4$-C$_{20}$ alkyl, C$_4$-C$_{20}$ alkenyl, C$_4$-C$_{20}$ alkynyl, carbocyclic radicals or heterocyclic radicals;
(b) is a member of (a) substituted with one or more independently selected non-interfering substituents;
(c) is the group —(L)—(R$_{80}$) where —(L)—is a divalent linking group of 1 to 12 atoms selected from carbon, hydrogen, oxygen, nitrogen, and sulfur wherein the combination of atoms in —(L)—are selected from the group consisting of (i) carbon and hydrogen only, (ii) sulfur only, (iii) oxygen only, (iv) nitrogen and hydrogen only, (v) carbon, hydrogen and sulfur only; and where R$_{80}$ is a group selected from (a) or (b);
(d) is a group having the formula:

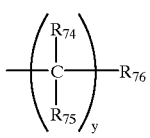

wherein
each R$_{74}$ and R$_{75}$ are independently selected from hydrogen, hydroxy, or C$_1$-C$_{10}$ alkyl, or R$_{74}$ and R$_{75}$ taken together are ===; R$_{76}$ is aryl or aryl substituted by halo, cyano, —CHO, hydroxy, nitro, phenyl, SH, C$_1$-C$_{10}$ alkyl, C$_1$-C$_{10}$ alkoxy, C$_1$-C$_{10}$ alkylthio, amino, hydroxyamino, or a 5 to 8 membered unsubstituted heterocyclic ring or substituted with non-interfering substituents;
y is 1 to 8;
R$_2$ is hydrogen, halo, C$_1$-C$_3$ alkyl, C$_2$-C$_3$ alkenyl, Cl-C$_2$ alkylthio, C$_1$-C$_3$ alkoxy, C$_2$-C$_3$ alkenyloxy, C$_2$-C$_3$ alkynyloxy, C$_3$-C$_4$ cycloalkyl, C$_3$-C$_4$ cycloalkenyl, cyano, —CHO, amino, amidino, carbamyl, carboxyl, methylsulfinyl, hydrazino, hydrazido, C$_1$-C$_2$ hydroxyalkyl, thiocarbonyl or C$_1$-C$_2$ carbonyl;
R$_3$ is

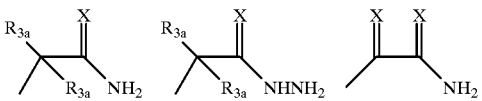

wherein
each R$_{3a}$ is independently hydrogen, halo, or C$_1$-C$_3$ alkyl and X is oxygen or sulfur;
R$_4$, R$_5$, R$_6$, R$_7$ are each independently hydrogen, phenoxy, halo, hydroxy, C$_1$-C$_{10}$ alkyl, C$_2$-C$_{10}$ alkenyl, C$_2$-C$_{10}$ alkynyl, C$_3$-C$_8$ cycloalkyl, aryl, aralkyl, C$_1$-C$_{10}$ haloalkyl, $C_1$-$C_{10}$ alkoxy, $C_1$-$C_{10}$ haloalkoxy, $C_4$-$C_8$ cycloalkoxy, $C_1$-$C_{10}$ alkylthio, arylthio, thioacetal, -C(O)O($C_1$-$C_{10}$ alkyl), carboxyl, hydrazide, hydrazino, hydrazido, amino, nitro, SH, cyano, —$NR_{82}R_{83}$ and —$C(O)NR_{82}R_{83}$, where $R_{82}$ and $R_{83}$ are independently hydrogen, $C_1$-$C_{10}$ alkyl, $C_1$-$C_{10}$ hydroxyalkyl, or taken together with N, form a 5 to 8-membered heterocyclic ring; or any two adjacent hydrocarbyl groups in the set $R_4$, $R_5$, $R_6$, $R_7$, combine with the ring carbon atoms to which they are attached to form a 5 or 6 membered unsubstituted carbocyclic ring, or substituted with a non-interfering substituent; or the group —($L_a$)—Q wherein —($L_a$)—is an acid linker having an acid linker length of 1 to 10 and Q is an acidic group or -C(O)$NR_{82}R_{83}$, wherein $R_{82}$ and $R_{83}$ are independently hydrogen, $C_1$-$C_{10}$ alkyl, $C_1$-$C_{10}$ hydroxyalkyl, or taken together with N, form a 5 to 8-membered heterocyclic ring.

3. The method of claim 2, wherein $R_4$ or $R_5$ are the group —($L_a$)—Q, wherein —($L_a$)—is an acid linker having the following formula;

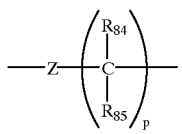

wherein,
$R_{84}$ and $R_{85}$ are each independently selected from hydrogen, $C_1$-$C_{10}$ alkyl, hydroxy, or $R_{84}$ and $R_{85}$ taken together are ═;
p is 1 to 8,
Z is a bond, O, N($C_1$-$C_{10}$ alkyl), N(H), or S.

4. The method of claim 1, wherein said inhibitor is administered systemically by an oral route.

5. The method of claim 1, wherein said inhibitor is administered directly to the periodontal pocket in a carrier comprised of a biocompatible polymeric material.

6. The method of claim 5, wherein said inhibitor is administered in a chewing gum carrier comprised of said polymeric material, wherein said polymeric material is selected from natural and synthetic elastomers.

7. The method of claim 1, wherein said inhibitor is administered directly to the periodontal pocket in a carrier comprised of an oral irrigation solution.

8. The method of claim 1, wherein said inhibitor is administered topically to the oral cavity in a carrier selected from a toothpaste carrier or mouthwash carrier.

9. The method of claim 1, wherein said inhibitor is administered in a carrier that includes an antibacterial agent.

10. The method of claim 1, wherein said inhibitor has the following structure:

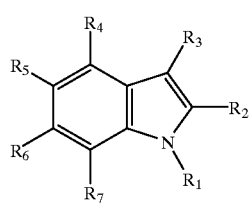

(I)

or a pharmaceutically acceptable salt or prodrug derivative thereof,
wherein $R_1$ is

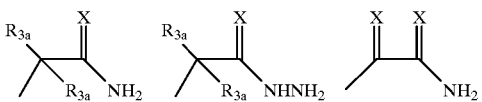

wherein
each $R_{3a}$ is independently hydrogen, halo or $C_1$-$C_3$ alkyl and X is oxygen or sulfur;
$R_2$ is hydrogen, halo, $C_1$-$C_3$ alkyl, $C_3$-$C_4$ cycloalkyl, $C_3$-$C_4$ cycloalkenyl, $C_1$-$C_2$ alkoxyl, $C_1$-$C_2$ alkylthio or a non-interfering substitutent selected from the group consisting of cyano, amino, amidino, halo, carbamyl, carboxyl, $C_2$-$C_3$ alkenyl, $C_1$-$C_3$ alkyl, cyclopropyl, cyclopropenyl, $C_1$-$C_3$ alkoxy, $C_1$-$C_2$ alkenyloxy, $C_2$-$C_3$ alkynyloxy, C, alkylsulfinyl, hydrazino, $C_1$-$C_2$ hydroxyalkyl, thiocarbonyl, and $C_1$-$C_2$ carbonyl;
$R_3$ is selected from groups (a), (b) and (c) wherein:
(a) is $C_7$-$C_{20}$ alkyl, $C_7$-$C_{20}$ alkenyl, $C_7$-$C_{20}$ alkynyl, carbocyclic radicals or heterocyclic radicals;
(b) is a member of (a) substituted with one or more independently selected non-interfering substituents; or
(c) is the group —(L)—$R_{80}$ wherein —(L)—is a divalent linking group of 1 to 12 atoms selected from carbon, hydrogen, oxygen, nitrogen, and sulfur wherein the combination of atoms in —(L)—are selected from the group consisting of (i) carbon and hydrogen only, (ii) sulfur only, (iii) oxygen only, (iv) nitrogen and hydrogen only, (v) carbon, hydrogen and sulfur only; and where $R_{80}$ is a group selected from (a) or (b);
$R_4$ and $R_5$ are each independently selected from hydrogen, non-interfering substituent, carbocyclic radical, carbocyclic radical substituted with non-interfering substituents, heterocyclic radical and heterocyclic radical substituted with non-interfering substituents;
$R_6$ an-d $R_7$ are independently selected from hydrogen, a non-interfering substituent, or the group —($L_a$)—(acidic group) wherein —($L_a$)—is an acid linker having an acid linker length of 1 to 10.

11. The method of claim 1, wherein said inhibitor has the following structure:

(II)

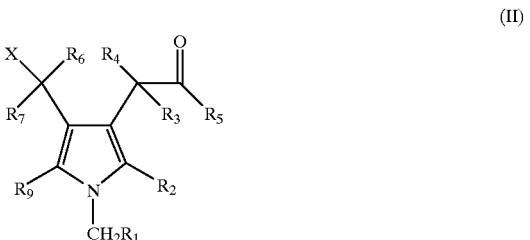

or a pharmaceutically acceptable salt thereof,
wherein
$R_1$ is hydrogen, $C_1$-$C_4$ alkyl, phenyl or phenyl substituted with one or two substituents selected from the group consisting of $C_1$-$C_4$ alkyl, $C_1$-$C_4$ alkoxy, phenyl($C_1$-$C_4$)alkyl, $C_1$-$C_4$ alkylthio, halo and phenyl;
$R_2$ is hydrogen, $C_1$-$C_4$ alkyl, halo, $C_1$-$C_4$ alkoxy, or $C_1$-$C_4$ alkylthio;
$R_3$ and $R_4$ are each hydrogen, or when taken together are ═;

$R_5$ is amino or $NHNH_2$;

$R_6$ and $R_7$ are each hydrogen; or when one of $R_6$ and $R_7$ is hydrogen, the other is $C_1$-$C_4$ alkyl or —$(CH_2)_nR_{10}$ wherein $R_{10}$ is —$CO_2R_{11}$, $PO_3(R_{11})_2$, —$PO_4(R_{11})_2$ or —$SO_3R_{11}$ wherein $R_{11}$ is independently hydrogen or $C_1$-$C_4$ alkyl and n is 1 to 4; or $R_6$ and $R_7$ taken together, are =O or =S:

X is $(C_1$-$C_6)$alkyl or $(C_2$-$C_6)$alkenyl which are substituted with $R_8$; or is phenyl substituted at the ortho position with $R_8$ or additionally optionally substituted with one or two substituents selected from the group consisting of hydrogen, $C_1$-$C_4$ alkyl, halo, $C_1$-$C_4$ alkoxy, or two substituents, when taken together with the phenyl group to which they are attached, form a naphthyl group; wherein $R_8$ is —$(CH_2)_r$—$R_{10}$ and $R_{10}$, $R_{11}$ and n are as defined above; and $R_9$ is hydrogen or $C_1$-$C_4$ alkyl.

12. A composition for treating periodontal disease in a mammal, comprising:
an effective amount of an inhibitor of secretory phospholipase $A_2$ in a carrier comprised of a biocompatible polymeric material.

13. The composition of claim 12, wherein said polymeric material is selected from the group consisting of glycolic acid polymers, methacrylate polymers, ethylene vinyl acetate copolymers, ethylene vinyl alcohol copolymers, polylactides and polycaprolactone.

14. The composition of claim 13, wherein said polymeric materials further include collagen and a cellulosic polymer and are in the form a fiber configured for delivery to the periodontal pocket.

15. The composition of claim 12, wherein said inhibitor is administered in a chewing gum carrier comprised of said polymeric material, wherein said polymeric material is selected from natural and synthetic elastomers.

16. The composition of claim 12, wherein said carrier is further selected from a toothpaste carrier and a mouthwash carrier.

17. The composition of claim 16, wherein said inhibitor has the following structure:

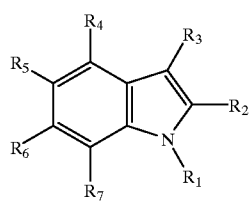

(I)

or a pharmaceutically acceptable salt, or prodrug derivative thereof
wherein
$R_1$ is selected from the groups (a), (b), (c) or (d) wherein:
(a) is $C_4$-$C_{20}$ alkyl, $C_4$-$C_{20}$ alkenyl, $C_4$-$C_{20}$ alkynyl, carbocyclic radicals or heterocyclic radicals;
(b) is a member of (a) substituted with one or more independently selected non-interfering substituents;
(c) is the group —(L)—$(R_{80})$ where —(L)—is a divalent linking group of 1 to 12 atoms selected from carbon, hydrogen, oxygen, nitrogen, and sulfur wherein the combination of atoms in —(L)—are selected from the group consisting of (i) carbon and hydrogen only, (ii) sulfur only, (iii) oxygen only, (iv) nitrogen and hydrogen only, (v) carbon, hydrogen and sulfur only; and where $R_{80}$ is a group selected from (a) or (b),
(d) is a group having the formula:

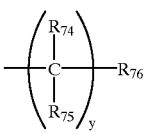

wherein
each $R_{74}$ and $R_{75}$ are independently selected from hydrogen, hydroxy, or $C_1$-$C_{10}$ alkyl, or $R_{74}$ and $R_{75}$ taken together are =O; $R_{76}$ is aryl or aryl substituted by halo, cyano, —CHO, hydroxy, nitro, phenyl, SH, $C_1$-$C_{10}$ alkyl, $C_1$-$C_{10}$ alkoxy, $C_1$-$C_{10}$ alkylthio, amino, hydroxyamino, or a 5 to 8 membered unsubstituted heterocyclic ring or substituted with a non-interfering substituent;

y is 1 to 8;

$R_2$ is hydrogen, halo, $C_1$-$C_3$ alkyl, $C_2$-$C_3$ alkenyl, $C_1$-$C_2$ alkylthio, $C_1$-$C_3$ alkoxy, $C_2$-$C_3$, alkenyloxy, $C_2$-$C_3$ alkynyloxy, $C_3$-$C_4$ cycloalkyl, $C_3$-$C_4$ cycloalkenyl, cyano, —CHO, amino, amidino, carbamyl, carboxyl, methylsulfinyl, hydrazino, hydrazido, $C_1$-$C_2$ hydroxyalkyl, thiocarbonyl or $C_1$-$C_2$ carbonyl;

$R_3$ is

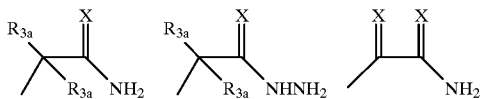

wherein
each $R_{3a}$ is independently hydrogen, halo, or $C_1$-$C_3$ alkyl and X is oxygen or sulfur;

$R_4$, $R_5$, $R_6$, $R_7$ are each independently hydrogen, phenoxy, halo, hydroxy, $C_1$-$C_{10}$ alkyl, $C_2$-$C_{10}$ alkenyl, $C_2$-$C_{10}$ alkynyl, $C_3$-$C_8$ cycloalkyl, aryl, aralkyl, $C_1$-$C_{10}$ haloalkyl, $C_1$-$C_{10}$ alkoxy, $C_1$-$C_{10}$ haloalkoxy, $C_4$-$C_8$ cycloalkoxy, $C_1$-$C_{10}$ alkylthio, arylthio, thioacetal, —C(O)O($C_1$-$C_{10}$ alkyl), carboxyl, hydrazide, hydrazino, hydrazido, amino, nitro, SH, cyano, $NR_{82}R_{83}$ and —C(O)$NR_{82}R_{83}$, where $R_{82}$ and $R_{83}$ are independently hydrogen, $C_1$-$C_{10}$ alkyl, $C_1$-$C_{10}$ hydroxyalkyl, or taken together with N, form a 5 to 8—membered heterocyclic ring; or any two adjacent hydrocarbyl groups in the set $R_4$, $R_5$, $R_6$, $R_7$ combine with the ring carbon atoms to which they are attached to form a 5 or 6 membered unsubstituted carbocyclic ring, or substituted with a non-interfering substituent; or the group —$(L_a)$—Q wherein —$(L_a)$—is an acid linker having an acid linker length of 1 to 10 and Q is and acidic group or —C(O)$NR_{82}R_{83}$, wherein $R_{82}$ and $R_{83}$ are independently hydrogen, $C_1$-$C_{10}$ alkyl, $C_1$-$C_{10}$ hydroxyalkyl, or taken together with N, form a 5 to 8-membered heterocyclic ring.

18. The composition of claim 17, wherein $R_4$ or $R_5$ are the group —$(L_a)$—Q, wherein —$(L_a)$—is an acid linker having the following structure:

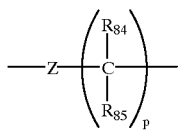

wherein,
$R_{84}$ and $R_{85}$ are each independently selected from hydrogen, $C_1$-$C_{10}$ alkyl, hydroxy, or $R_{84}$ and $R_{85}$ taken together are ===;
p is 1 to 8, and
Z is a bond, O, N($C_1$-$C_{10}$ alkyl), N(H), or S.

19. The composition of claim 17, wherein said composition further includes an antibacterial agent.

20. The composition of claim 16, wherein said inhibitor has the following structure:

(I)

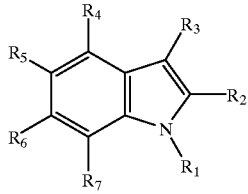

or a pharmaceutically acceptable salt or prodrug derivative thereof,
wherein
$R_1$ is

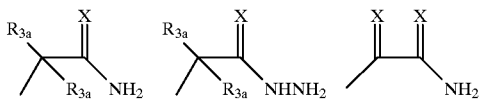

wherein
each $R_{3a}$ is independently hydrogen, halo or $C_1$-$C_3$ alkyl and X is oxygen or sulfur;
$R_2$ is hydrogen, halo, $C_1$-$C_3$ alkyl, $C_3$-$C_4$ cycloalkyl, $C_3$-$C_4$ cycloalkenyl, $C_1$-$C_2$ alkoxyl, $C_1$-$C_2$ alkylthio or a non-interfering substitutent selected from the group consisting of cyano, amino, amidino, halo, carbamyl, carboxyl, $C_2$-$C_3$ alkenyl, $C_1$-$C_3$ alkyl, cyclopropyl, cyclopropenyl, $C_1$-$C_3$ alkoxy, $C_1$-$C_2$ alkenyloxy, $C_2$-$C_3$ alkynyloxy, C, alkylsulfinyl, hydrazino, $C_1$-$C_2$ hydroxyalkyl, thiocarbonyl, and $C_1$-$C_2$ carbonyl;
$R_3$ is selected from groups (a), (b) and (c) wherein:
(a) is $C_7$-$C_{20}$ alkyl, $C_7$-$C_{20}$ alkenyl, $C_7$-$C_{20}$ alkynyl, carbocyclic radicals or heterocyclic radicals;
(b) is a member of (a) substituted with one or more independently selected non-interfering substituents; or
(c) is the group —(L)—$R_{80}$ wherein —(L)—is a divalent linking group of 1 to 12 atoms selected from carbon, hydrogen, oxygen, nitrogen, and sulfur wherein the combination of atoms in —(L)—are selected from the group consisting of (i) carbon and hydrogen only, (ii) sulfur only, (iii) oxygen only, (iv) nitrogen and hydrogen only, (v) carbon, hydrogen and sulfur only and where $R_{80}$ is a group selected from (a) or (b);
$R_4$ and $R_5$ are each independently selected from hydrogen, non-interfering substituent, carbocyclic radical, carbocyclic radical substituted with non-interfering substituents, heterocyclic radical and heterocyclic radical substituted with non-interfering substituents;
$R_6$ and $R_7$ are independently selected from hydrogen, a non-interfering substituent, or the group —($L_a$)—(acidic group) wherein —($L_a$)—is an acid linker having an acid linker length of 1 to 10, provided that at least one of $R_6$ and $R_7$ must be the group —($L_a$)—(acidic group).

21. The composition of claim 20, wherein said composition further includes an antibacterial agent.

22. The composition of claim 16, wherein said inhibitor has the following structure:

(II)

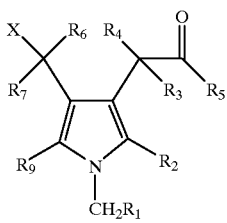

or a pharmaceutically acceptable salt thereof,
wherein
$R_1$ is hydrogen, —($C_1$-$C_4$) alkyl, phenyl or phenyl substituted with one or two substituents selected from the group consisting of $C_1$-$C_4$ alkyl, $C_1$-$C_4$ alkoxy, phenyl ($C_1$-$C_4$)alkyl, $C_1$-$C_4$ alkylthio, halo and phenyl;
$R_2$ is hydrogen, $C_1$-$C_4$ alkyl, halo, $C_1$-$C_4$ alkoxy, or $C_1$-$C_4$ alkylthio;
$R_3$ and $R_4$ are each hydrogen, or when taken together are ===;
$R_5$ is amino or-NHNH$_2$;
$R_6$ and $R_7$ are each hydrogen; or when one of $R_6$ and $R_7$ is hydrogen, the other is $C_1$-$C_4$ alkyl or $(CH_2)_n$—$R_{10}$ wherein $R_{10}$ is $CO_2R_{11}$, $PO_3(R_{11})_2$, $PO_4(R_{11})_2$ or $SO_3R_{11}$ wherein $R_{11}$ is independently hydrogen $C_1$-$C_4$ alkyl and n is 1 to 4; or $R_6$ and $R_7$, taken together, are =O or =S;
X is ($C_1$-$C_6$)alkyl or ($C_2$-$C_6$)alkenyl which are substituted with $R_8$; or is phenyl substituted at the ortho position with $R_8$ or additionally optionally substituted with one or two substituents selected from the group consisting of hydrogen, $C_1$-$C_4$ alkyl, halo, $C_1$-$C_4$ alkoxy, or two substituents, when taken together with the phenyl group to which they are attached, form a naphthyl group; wherein $R_8$ is —$(CH_2)_n$—$R_{10}$ and $R_{10}$, $R_1$, and n are as defined above; and
$R_9$ is hydrogen or $C_1$-$C_4$ alkyl.

23. The composition of claim 22, wherein said composition further includes an antibacterial agent.

24. A device for treating periodontal disease in a mammal, comprising:
a matrix sized for introduction into a periodontal pocket for treatment of periodontal disease, said matrix impregnated with an effective amount of an inhibitor of secretory phospholipase $A_2$.

* * * * *

UNITED STATES PATENT AND TRADEMARK OFFICE
CERTIFICATE OF CORRECTION

PATENT NO.    : 6,325,991 B1
DATED         : December 4, 2001
INVENTOR(S)   : Susan E. Draheim It is certified that error appears in the above-identified patent and that said Letters Patent is hereby corrected as shown below:

Please change "≡" to -- ≡O -- at the following locations:

Column 6, line 35
Column 8, line 17
Column 9, line 55
Column 14, lines 26 and 33
Column 20, line 41
Column 21, line 32
Column 22, line 67
Column 23, line 7
Column 24, line 16
Column 25, line 11
Column 26, line 38.

Signed and Sealed this

Eleventh Day of June, 2002

Attest:

Attesting Officer

JAMES E. ROGAN
Director of the United States Patent and Trademark Office